United States Patent [19]

Carlon et al.

[11] Patent Number: 5,059,350
[45] Date of Patent: Oct. 22, 1991

[54] METHOD OF TESTING THE EFFICIENCY OF GAS MASK FILTERS USING POLY-ALPHA OLEFIN AEROSOL MIXTURES

[75] Inventors: Hugh R. Carlon, Fallston; Mark A. Guelta, White Marsh; Bernard V. Gerber, Havre de Grace, all of Md.

[73] Assignee: The United States of America as represented by the Secretary of the Army, Washington, D.C.

[21] Appl. No.: 636,160

[22] Filed: Dec. 31, 1990

[51] Int. Cl.$^5$ .............................................. G01N 31/00
[52] U.S. Cl. .................................. 252/408.1; 252/305; 73/40; 356/336
[58] Field of Search .................. 252/408.1, 305; 73/40; 356/336

[56] References Cited

U.S. PATENT DOCUMENTS

H267    5/1987  Carlton et al. ...................... 356/336
4,914,957 4/1990 Dougherty .............................. 73/40
4,917,830 4/1990 Ortiz et al. .......................... 261/18.1
4,963,289 10/1990 Ortiz et al. .......................... 252/305

Primary Examiner—Robert L. Stoll
Assistant Examiner—N. Bhat
Attorney, Agent, or Firm—Anthony T. Lane; Edward Goldberg; Edward F. Costigan

[57] ABSTRACT

An improved process of passing an aerosol mixture through a filter. The aerosol mixture solely being a poly alpha olefin having a content of hydrocarbon % by volume of:

|    | %    | Carbon atoms, chain length |
|----|------|----------------------------|
| A. | 30.9 | 30                         |
| B. | 42.8 | 40                         |
| C. | 20.4 | 50                         |
| D. | 4.8  | 60                         |
| E. | 1.1  | 70.                        |

5 Claims, 1 Drawing Sheet

FLOW DIAGRAM TDA-100

FLOW DIAGRAM TDA-100

METHOD OF TESTING THE EFFICIENCY OF GAS MASK FILTERS USING POLY-ALPHA OLEFIN AEROSOL MIXTURES

GOVERNMENTAL INTEREST

The invention described herein may be made, used or licensed by or for the Government for governmental purposes without the payment to us of any royalties thereon.

FIELD OF USE

An improved method of testing a filter for gas masks, respirators, and personnel protective equipment.

BACKGROUND OF THE INVENTION

The present invention relates to a method for the generation of a nearly monodispersed aerosol in filter-testing penetrometer machines.

The present invention is superior to the previous process in that it employs a candidate mixture as a replacement for dioctyl phthalate (DOP), which is a suspected carcinogen. In the following discussion, the term "Candidate Material" will be used to designate an aerosol mixture made up of the following: poly alpha olefin having chain lengths in percentages of about, by volume, of 30.9% of 30 carbon atoms, 42.8% of 40 carbon atoms, 20.4% of 50 carbon atoms, 4.8% of 60 carbon atoms, and 1.1% of 70 carbon atoms. The term poly alpha olefin in this case is called also a synthetic hydrocarbon 6 CST fluid. The CST refers to centistokes, a measure of viscosity. The number ahead of CST fluid specifies the viscosity at 100 degrees C. The candidate mixture is manufactured by Henkel Corporation, Emery Group, 11501 Northlake Drive, P.O. Box 429557, Cincinnati, OH 45249. The candidate mixture has been identified by us as a thermally stable material of low toxicity.

For several decades, the U.S. Army has produced hot smokes using DOP as the standard material in the performance of nondestructive gas mask and filter serviceability testing. Hot smokes are aerosols produced using a method of thermally-generated vaporization and re-condensation (self nucleation) of particles. Heated air passes across the surface of a heated liquid (DOP); cooler air then merges with the vapor causing recondensation of an aerosol or "hot smoke." The U.S. Army Surgeon General has designated DOP as a suspected carcinogen and has prohibited or severely restricted its use in smoke-generating machines used to test U.S. Army masks, respirators, filters, and other personnel protection equipment.

The ATI model TDA-100 (Q-127) monodispersed filter penetrometer is manufactured by Air Techniques, Inc. (ATI), a Division of Hamilton Associates, Inc., 1716 Whitehead Road, Baltimore, MD 21207. A description of this equipment is given elsewhere in this disclosure. Thus, the candidate material and process have been shown to be acceptable to the manufacturer for specification in his new machines.

SYSTEM OVERVIEW

Figure 1:
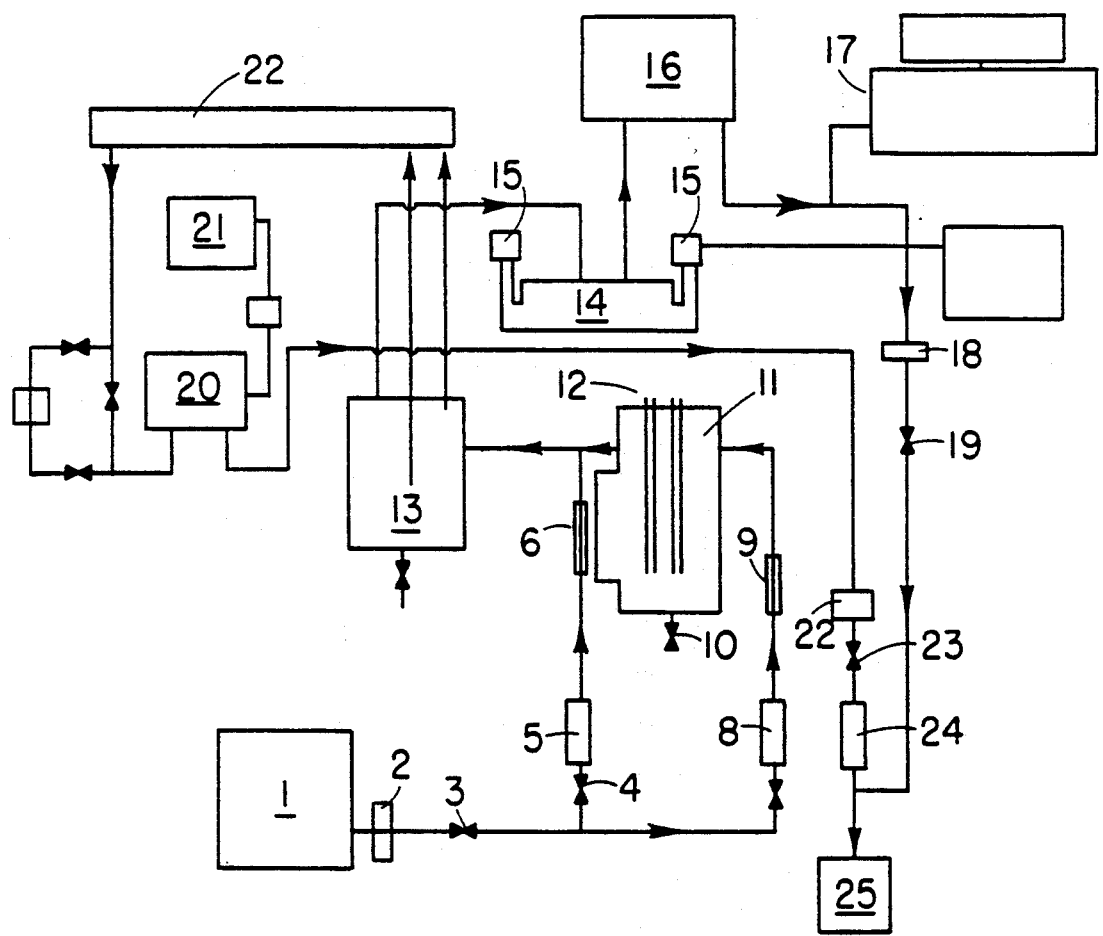
FIG. 1 is a diagram showing flow paths for aerosol generation, measurement, and filter test flows in the TDA-100 machines.

The TDA-100 machine produces hot smoke by passing a heated air stream across a heated reservoir, collecting vapor from DOP or the heated candidate material. This vapor stream merges with a cooler quenching air stream which causes the vapor to condense into an aerosol of particles in the submicron size range. The aerosol mean particle size, width of distribution, and mass concentration is controlled by the temperature and volume ratios of the air streams and the temperature of the heated DOP or candidate material. The recondensed aerosol passes into an aging chamber to allow uniform mixing of the aerosol. From the aging chamber, a sample of the aerosol is piped to an optical nephelometer called a mechanical owl which indicates mean particle size by the intensity ratio of mutually perpendicular components of polarized scattered light viewed at an angle of 90 degrees from the incident beam. From the mechanical owl analyzer, the aerosol is piped to a "LAS-X" laser aerosol spectrometer. The LAS-X is manufactured by Particle Measuring Systems, Inc., 1855 South 57th Court, Boulder, Colorado 80301. The LAS-X contains a precision laser illuminating system which allows single particle sizing by collecting the light scattered from each particle. The particle scattering pulses from the photodetector are converted into a corresponding size category for accumulation in the data logging electronics. This data is transferred to the Hewlett Packard 85 (HP-85) microcomputer. The HP-85 determines the mean particle size, expressed as geometric mean diameter (GMD), and width of particle distribution, expressed as geometric standard deviation (GSD). Aerosol from the aging chamber is also piped to the filter test chuck for filter efficiency analysis. The chuck is a pneumatically-operated device which holds and seals the filter canister to be tested. Aerosol passing through the filter flows through a light scattering chamber. Measurement of scattered light intensity upstream and downstream of the filter indicates the percent of the original aerosol which passes through the filter, i.e., the filter's efficiency.

SYSTEM OPERATION

Air for smoke production is generated by a blower contained within the instrument (1, FIG. 1). The air generated by the blower is filtered before use by an in-line air filter (2, FIG. 1). Filtered air for producing smoke is regulated by a pressure regulator (3, FIG. 1), set to 6 psi. Immediately downstream of the pressure regulator, the air stream splits, one portion is used for vapor pick-up air, the other for vapor quench air.

The vapor pick-up air is controlled by a needle valve (7, FIG. 1). The flow is read from a flowmeter (8, FIG. 1). The vapor pick-up flow has an adjustment range of 0 to 30 liters per minute (LPM). Newer TDA-100 models may have a broader adjustment range. After passing through the flowmeter, the vapor pick-up air is heated by the in-line vapor pick-up air heating element (9, FIG. 1). The heating element receives a voltage adjusted to maintain a vapor air temperature of 165° C. The vapor pick-up air stream passes over the heated candidate material before it merges with the quench air.

The quench air control valve (4, FIG. 1) controls the air flow. The quench air flow rate can be adjusted from 0–100 LPM. The flow rate is read on the quench air flowmeter (5, FIG. 1). An in-line heating element (6, FIG. 1) controls the quench air temperature. A variac controller is used to adjust the voltage to the quench air heating element and control particle size. The voltage range is variable from 0–110 volts.

The candidate material operating temperature is maintained in the "hot pot" (10, FIG. 1) by a liquid heating element (11, FIG. 1). A thermocouple (12, FIG. 1) automatically monitors the candidate material temperature. An Athena thermoregulator automatically controls the candidate material temperature.

After the vapor pickup air and the quench air merge, the recondensed smoke mixes in the aging chamber (13, FIG. 1). From the aging chamber, the smoke can exit through three pipes:

1. The smoke is piped to the owl for particle sizing.
2. The smoke is piped to the chuck to be used in filter penetration testing.
3. The remaining smoke which is not used for sizing or testing is vented.

A portion of the smoke from the aging chamber is drawn through the "mechanical owl" (14, FIG. 1) to be used in smoke particle sizing. The "mechanical owl" consists of a smoke chamber with photomultiplier tubes at each end to view the white light scattered at right angles to a collated beam passing through the chamber. Before reaching each photomultiplier tube, the light is passed through a fixed polaroid disk and a rotatable polaroid disk. The fixed disks at each end are arranged with their axes of polarization at right angles to each other. The rotatable disks are totatively geared together with parallel axes of polarization. The angle of rotation relative to one of the fixed disks is measured on a vernier protractor scale. A calibration procedure is available to match the photomultiplier tube gains. In use, the signal outputs are substracted and the result read on a meter. For a particular angular setting of the paired rotatable polaroids, a null meter reading indicates equal scattered light intensity viewed through the two polaroid disks with mutually perpendicular axes of polarization. This angle has been uniquely correlated to particle size of monodisperses liquid smoke particles in the sub-micron range.

In our research, a second method of particle sizing was used. This method will not be available to operators in the field. This second method of sizing gives a direct reading of the frequency of aerosol particle sizes in a number of contiguous size intervals while the mechanical owl reading above only indicates an average size. The method of indicating particle size with the mechanical owl rather than measuring a particle size with a LAS-X has been used by operators for decades. As long as the recommended machine settings are used, the size indication from the owl is acceptable. In the past, recommended machine settings and the owl measurement have been the operator's only means of controlling aerosol GMD.

Candidate material smoke is drawn from the outlet of the mechanical owl analyzed through a TSI model 3302 capillary diluter (16, FIG. 1). The capillary diluter dilutes the smoke from the mechanical owl by a factor of 2000:1. A portion of the diluted smoke is piped to the LAS-X. The LAS-X laser aerosol spectrometer makes particle histogram measurements on the diluted smoke which are then analyzed and the results printed using the Hewlett Packard Microcomputer (17, FIG. 1). This system measures and prints smoke GMD and GSD. Smoke from the capillary diluter which is not used by the LAS-X is filtered by an in-line high efficiency filter (18, FIG. 1). The flow rate of sample smoke is controlled by the sample control valve (19, FIG. 1). The cleaned sample air is then exhausted via the vacuum source. (25, FIG. 1).

Smoke for filter testing is drawn from the aging chamber through the chuck (22, FIG. 1). Relative smoke concentration is measured downstream of the test chuck by a light scattering chamber (20, FIG. 1.) Filter penetration is measured in percent. The relative 100% point is set by closing the chuck and allowing the concentrated smoke to be sampled by the penetrometer (20, FIG. 1). The penetration indicator is zeroed by opening the chuck and allowing clean air to be sampled by the penetrometer. The penetration indicator (21, FIG. 1) indicates percent penetration through the test filter. Smoke remaining in the test air stream after filter tests or penetrometer setup is filtered by a in-line HEPA filter. Filter resistance is indicated by the filter resistance gauge. The test air flow is controlled by a valve (23, FIG. 1). Test air flow is indicated by test air flowmeter (24, FIG. 1). Test air is exhausted via a vacuum pump (25, FIG. 1) contained in the TDA-100.

RECOMMENDED MACHINE SETTINGS

The following machine parameters were found in our process to produce an aerosol, using our candidate material, which gave the same or better test smoke performance as those measured experimentally using DOP. Actual settings may differ slightly between machines.

| | |
|---|---|
| Candidate material temperature | 195 degrees C. |
| "Owl" Setting | 35 degrees |
| Particle size control | 85–90 volts |
| Vapor Pick-up Flow | 10 LPM |
| Quench Air Flow | 90 LPM |

A candidate material temperature of 195° C. was found to produce a mass concentration of approximately 110 mg/m$^3$. To obtain higher concentrations, the candidate material temperature was raised. An "Owl" setting of 35 degrees and the above vapor pick-up air/quench air ratios generated GMDs of 0.2 micrometers ($\mu$m) with GSDs of approximately 1.23. These specifications met or exceeded those obtained using DOP, and were within the U.S. Army test requirements of 0.18–0.33 $\mu$m GMD and GSD of $<1.30$.

PENETROMETER

The TDA-100 Monodispersed Aerosol Penetrometer incorporates the most advanced technology of unique design to make a 0.3 micrometer nearly monodispersed aerosol, measure and control the aerosol particle size and concentration plus measure the percent penetration of the tested component by the aerosol.

The TDA-100 is a basic apparatus consisting of three major components. They are:

1. The penetrometer itself consisting of the aerosol making and controlling equipment.
2. The particle size indicator and the mechanical analyzer which monitor the aerosol particle size.
3. The percent penetration indicator and associated light scattering chamber which measures the percent of aerosol penetrating the component being tested.

There are many adaptations and possibilities for various chuck and test fixtures which enable testing of a great variety of samples ranging from flat material to highly complex respirators.

In general, the TDA-100 operates as follows:

Compressed air, passing through a filter and moisture trap, is connected to the penetrometer and regulated to a pressure of 6 pounds per square inch gage (psig). The air is then divided into two streams, vapor and diluent. The vapor stream flows at 20 liters per minute through a preheater, then into an aerosol generator and over the surface of liquid which is maintained at 195°±2° C. The diluent stream is cooled by a vortex tube and then heated by an electrical element. It bypasses the aerosol generator at a flow rate of 80 liters per minute and joins the vapor stream on the outlet side of the generator to make an aerosol. The aerosol is passed into an aging chamber where it is stabilized. During testing, aerosol flows from the aging chamber to the chuck or test fixture adaptation and through the component under test, such as a filter. As aerosol is continually being made when the penetrometer is operating and testing is intermittent, the excess aerosol is exhausted to the atmosphere from the aging chamber. The aerosol particle size is maintained at a predetermined level by controls on the penetrometer and is monitored by the aerosol particle size indicator. This indicator electronically measures aerosol particle size from a sample of the aerosol continually passing through a mechanical analyzer. This mechanical analyzer measures aerosol particle size by the degree of polarization of a light beam which passes through a sample of the aerosol. The particle size of the aerosol is controlled by adjusting the temperature of the diluent air stream.

A sample under test is subject to a concentration of aerosol of approximately 100 micrograms per liter. Using this concentration as a base line of 100%, the amount of aerosol penetrating the sample under test is measured by the percent penetration indicator. Such measurements are registered linearly on the meter. The specifications for the apparatus should be as follows:

1. Aerosol Generator: Produces 0.20 micron aerosol at a concentration of 100 micrograms/liter.
2. Vapor Flowmeter: Ranges from 5–50 SLPM @ 6 PSIG.
3. Diluent Flowmeter: Ranges from 10–100 SLPM @ 6 PSIG.
4. Test Flowmeter: Ranges from 16–85 SLPM @ a vacuum head of 5"HG.
5. Resistance Indicator: Optional.
6. Mechanical Analyzer: Measures light-angle refraction from 0–50 with four Polaroid and three condensing lenses.
7. Particle Size Indicator: Solid state type, capable sensitivity of ten divisions to 1 rotation of Mechanical Analyzer, approximate size—14"×8"×8".
8. Scattering Chamber: Forward light scattering, approximately 5"×5"×20" in size, with no dimming control and filter factor.
9. Percent Penetration Meter: Solid state type with ranges of 100%, 10%, 1%, 1%, 01%. Approximate size—14"×8"×8". Three place digital read out optional.
10. Vortex Tube: 5 cubic feet per min. capacity.
11. Mixing Chamber: Containing baffles with ports for exhaust, sample, inlet and test sample.
12. Vacuum Pump: Capable of delivering up to 85 SLPM L@ 5" HG pneumatic, silent operating type.
13. Air Operated Chuck: Manufactured to house customers' canisters of varying sizes, etc., to be tested.
14. Constant Voltage Regulator: 250 VA rating. Input of 95–130 VAC output of 118 VAC 0.5%.
15. Control Panel: Consisting of master "ON-OFF" particle size control, solid state time proportioning liquid temperature control, chuck control switches.

AEROSOL MEASUREMENTS

The following information is provided (1) to clarify how aerosol particle size distributions are represented, (2) to give U.S. Army smoke aerosol specifications for filter-testing penetrometer machines used to test respirators and mask canisters, and (3) to compare typical performance obtained using dioctyl phthalate (DOP) in our penetrometer machine with that obtained by us using our replacement material in our penetrometer machine using our process as described herein.

The U.S. Army requires these test smokes (aerosols) to meet these specifications:

(1) The geometric mean diameter (GMD), in micrometers ($\mu$m), of the aerosol must lie between 0.18 $\mu$m and 0.33 $\mu$m. This is the count or number mean of the distribution. That is, all particles in all size ranges are counted, and a distribution is drawn showing the total number of particles in all ranges (a histogram). From this, a mean size is determined.

(2) The geometric standard deviation (GSD) of the distribution must not exceed 1.30. The GSD is a measure of the narrowness (width) or "monodispersity" of the particle size distribution. An aerosol of particles of all one size would have a GSD=1.00. This is impossible to achieve even with latex spheres that are used to calibrate the instruments. The specified upper limit of GSD=1.30 insures that the width of the distribution is adequately narrow for desired tests. By comparison, aerosols produced by spraying (without vaporation and recondensation) often have GSDs of 2.00 or more.

(3) The smoke concentration at the test chuck where filter canisters are inserted must be 100 mg/m$^3$ plus or minus 20 mg/m$^3$. Concentrations that are too high can be reduced by process control adjustments. But good DOP replacement smokes should produce at least 80 mg/m$^3$ of smoke at the chuck.

In conclusion, an improved method of measuring the efficiency of a particulate filter as described herein has been shown. This is accomplished by passing an aerosol through a filter and measuring the percent penetration. Aerosol particle size is measured as geometric mean diameter by utilizing conventional equipment.

What is claimed is:

1. In an improved process of passing an aerosol mixture through a filter, the improvement consisting essentially of said aerosol being 30.9% by volume of a poly-alpha olefin having a chain length of 30 carbon atoms, 42.8% by volume of a poly-alpha olefin having a chain length of 40 carbon atoms, 20.4% by volume of a poly-alpha olefin having a chain length of 50 carbon atoms, 4.8% of a poly-alpha olefin having a chain length of 60 carbon atoms, and 1.1% of a poly-alpha olefin having a chain length of 70 carbon atoms.

2. The process of claim 1 wherein the concentration of said aerosol at said filter is 100 mg/m$^3$ plus or minus 20 mg/m$^3$.

3. The process of claim 1 wherein said measuring is done by light-scattering means.

4. The process of claim 1 wherein the geometric mean diameter of the aerosol mixture is about 0.20–0.30 micrometers.

5. The process of claim 1 wherein the geometric standard deviation of the aerosol mixture is about 1.25.

* * * * *